United States Patent [19]

Lammintausta et al.

[11] Patent Number: 4,783,477

[45] Date of Patent: Nov. 8, 1988

[54] ANXIOLYTIC COMPOSITION

[75] Inventors: Risto Lammintausta, Turku; Raimo Virtanen, Rusko, both of Finland

[73] Assignee: Farmos-Yhtyma Oy, Turku, Finland

[21] Appl. No.: 117,876

[22] Filed: Nov. 9, 1987

[30] Foreign Application Priority Data

Nov. 11, 1986 [FI] Finland .................. 864570

[51] Int. Cl.⁴ .......................................... A61K 31/415
[52] U.S. Cl. .................................................. 514/396
[58] Field of Search ......................................... 514/396

[56] References Cited

PUBLICATIONS

Chem. Abst. 105-183977 C (1986).

Primary Examiner—Stanley J. Friedman
Attorney, Agent, or Firm—Armstrong, Nikaido, Marmelstein & Kubovcik

[57] ABSTRACT

Medetomidine is useful in the treatment of anxiety disorders.

3 Claims, No Drawings

ANXIOLYTIC COMPOSITION

This invention relates to anxiolytic compositions, i.e. compositions useful in the therapy of anxiety.

Medetomidine or 4(5)-[α-methyl-2,3-dimethylbenzyl]imidazole, which has the formula

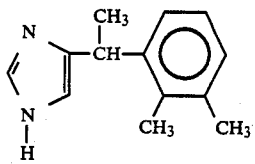

is a selective and potent $\alpha_2$-receptor agonist. It has been disclosed, e.g. in European Patent Publication No. 72615, as an antihypertensive agent and in European Patent Publication No. 187 471 as a veterinary sedative-analgesic agent in particular for small animals.

We have now found that this compound also possesses anxiolytic effects.

Anxiety disorder is a rather wide concept including, e.g., general anxiety, panic disorder and various kinds of withdrawal symptoms.

The effects of medetomidine on general anxiety have been studied using a method disclosed in Stuart Fielding and Harbans Lal, "Anxiolytics", Futura Publishing Co. Inc., Mount Kisco, N.Y., U.S.A., 1979. This method is well known from the study of benzodiazepines, and it is known to exhibit a very good correlation with results from clinical tests.

The test which we used is as follows:

Rats are deprived of water for 40 hours. At the appropriate time after dosing with the drug or vehicle control, a rat is placed in a test chamber. Water is made available through a stainless steel spout located on the back wall of the chamber. After locating the source of water, the rat is allowed 30 seconds of free (no shock) drinking. A circuit is then activated which applies an electric shock through the drinking spout.

In the tests with medetomidine, rats were trained to drink in the test chamber after 40 hr of water deprivation for three days. At the beginning of the test session, the animals were allowed to drink for 30 seconds without shocks and the number of licks was recorded as an estimate of nonpunished drinking. The shock level was adjusted so that normal animals got 5-10 shocks while drinking for 3 minutes. Medetomidine given at doses of 0.75, 1.5 and 3 0 μg/kg (i.p. 30 min before test) increased punished drinking by 82, 128 and 89% ($p<0.05$) respectively. For comparison purposes diazepam at a dosage of 5 mg/kg was found to increase punished drinking by 111% ($p<0.01$). In a different experiment medetomidine at doses of 3.0 and 9.0 μg/kg and diazepam at a dose of 5 mg/kg increased punished drinking by 71, 169 and 101% respectively ($p<0.01$). Medetomidine produced sedation after 30 μg/kg but not after 10 μg/kg. Medetomidine at doses of 1.0, 3.0 and 9.0 μg/kg antagonizes the proconflict effect of pentylenetetrazole (15 mg/kg i.p. 15 min before test, low shock level) by 40, 53 and 97% ($p<0.01$) respectively.

Medetomidine was administered to rats by microinfusion using a s.c. osmotic minipump for two weeks and the animals were tested on the 14th day. An infusion rate of 30 μg/kg/hr caused sedation whereas 10 μg/kg/hr had no effect on rotarod performance or spontaneous motility. Medetomidine (at 3 and 9 μg/kg/hr) increased punished drinking by 280% ($p<0.001$) and 115% ($p<0.05$) respectively over saline infusion rats, whereas 1 μg/kg/hr had no effect. In a withdrawal experiment the minipumps (3 μg/kg/hr) were removed 48 hr before the test. These animals showed a further increase in punished drinking by 131 and 221% ($p<0.001$) respectively compared to animals which were still receiving medetomidine or saline infusions respectively. Also the nonpunished drinking was increased in withdrawing animals, suggesting nonspecific stimulation.

These results indicate that medetomidine has significant anticonflict efficacy in rats after both a single or prolonged dosing.

It is well known that withdrawal symptoms are due to noradrenergic hyperactivity. Such symptoms can therefore be successfully treated with drugs which reduce the level of noradrenaline, e.g. clonidine. Experiments in the rat, carried out by us, indicate that medetomidine is able to reduce noradrenaline release and thus sympathetic tone both in the central and peripheral nervous systems. This has been clearly demonstrated by measuring the plasma concentrations of MHPG-$SO_4$ (the principal metabolite of central noradrenaline) in the rat after medetomidine administration.

TABLE 1

| Medetomidine dose μg/kg intraperitoneally | Brain MHPG-$SO_4$ ng/ml (4 h after medetomidine adm.) |
|---|---|
| 0 | 125 |
| 10 | 110 |
| 30 | 90 |
| 100 | 70 |
| 300 | 65 |

In healthy human volunteers very low medetomidine doses produce a drastic decrease in plasma noradrenaline concentrations reflecting the ability of the compound to decrease noradrenergic tone in man also, as shown in the following Table II.

TABLE II

| Medetomidine dose μg | Plasma noradrenaline nmol/l |
|---|---|
| 0 | 1.4 |
| 20 | 0.8 |
| 40 | 0.6 |
| 80 | 0.5 |
| 120 | 0.3 |

Medetomidine forms acid addition salts with both organic and inorganic acids. It can thus be used in the form of a pharmaceutically usable acid addition salt, as, for instance, the chloride, bromide, sulfate, nitrate, phosphate, sulfonate, formate, tartrate, maleate, citrate, benzoate, salicylate, ascorbate and the like.

A medetomidine-containing medicament of the present invention may be a pharmaceutical composition comprising medetomidine or a non-toxic, pharmaceutically acceptable salt thereof, and a compatible pharmaceutically acceptable carrier therefor.

Medetomidine, as the free base or as a non-toxic, pharmaceutically acceptable acid salt, may be administered parenterally, intravenously or orally. Typically, an effective amount of medetomidine is combined with a suitable pharmaceutical carrier. As used herein, the term "effective amount" encompasses those amounts which yield the desired anxiolytic activity without causing adverse side-effects. The precise amount employed is dependent upon numerous factors such as route of administration and type (species, age and size) of mammal.

A suitable dosage for an adult is usually in the range of 1 to 30 µg, preferably 2 to 10 µg, per day, by injection, while a suitable dosage for oral administration may be, e.g., 5 to 100 µg per day.

The pharmaceutical carriers which are typically employed with medetomidine may be solid or liquid and are selected with the planned manner of administration in mind. Thus, for example, solid carriers include lactose, sucrose, gelatin and agar, while liquid carriers include water, syrup, peanut oil and olive oil. Other suitable carriers are well-known to those skilled in the art of pharmaceutical formulations. The combination of the derivative and the carrier may be fashioned into numerous acceptable forms, such as tablets, capsules, suppositories, solutions, emulsions, and powders.

We claim:

1. Method for the treatment of an anxiety disorder which comprises administering to a subject suffering from such a disorder an effective amount of medetomidine.

2. Method according to claim 1 in which from 1 to 30 ug medetomidine is administered by injection per day to said subject.

3. Method according to claim 1 in which said anxiety disorder is general anxiety, panic disorder, or withdrawal symptoms.

* * * * *